United States Patent [19]

James

[11] Plant 5,073

[45] Jul. 26, 1983

[54] ALMOND TREE ("MESA")

[76] Inventor: Leonard D. James, 4017 Tully Rd., Modesto, Calif. 95356

[21] Appl. No.: 369,845

[22] Filed: Apr. 19, 1982

[51] Int. Cl.[3] ..... A01H 5/03
[52] U.S. Cl. ..... Plt./30
[58] Field of Search ..... Plt./30

*Primary Examiner*—Robert E. Bagwill
*Attorney, Agent, or Firm*—Roger B. Webster

[57] ABSTRACT

An almond tree which is open, large, vigorous, and upright; foliated with medium size, acuminate, acutely pointed leaves having a crenate margin, and alternate, small, globose, green glands; blooms early and heavily with white flowers; and is a regular, very heavy bearer of early-in-harvest, well-distributed nuts; the nuts, of medium size, being ovate, plump, soft shell, and well-sealed, and the kernels, of small but uniform size, being ovate, medium thick, and attractive in appearance.

1 Drawing Figure

BACKGROUND OF THE VARIETY

1. Field of the Invention

In the course of the maintenance of an almond orchard on my ranch located near Modesto, Stanislaus County, Calif., I frequent such orchard for the purpose of inspection, cultivation, and irrigation, and—against the background of such activities—the present variety of almond tree was discovered.

2. Classification of the Variety

The present new and distinct variety of almond tree is embraced by Class 30, Plants, of the United States Patent Office Manual of Classification.

3. Prior Varieties

Among the existent varieties of almond trees which are known to me, and mentioned herein, are Nonpareil and Mission (both unpatented).

ORIGIN OF THE VARIETY

The present variety of almond tree was discovered by me—during my activities in the maintenance of my almond orchard located as aforesaid—growing, in a corner of such orchard, as an open-pollinated, chance seedling. Upon observing the vigorous, upright growth of such chance seedling, together with its early bloom-time and certain beneficial nut characteristics, I asexually reproduced such chance seedling in anticipation of its potential as a commercial variety.

ASEXUAL REPRODUCTION OF THE VARIETY

The present variety of almond tree was asexually reproduced, by me, by grafting on an almond seedling, and, in maturity, such reproduction ran true to the original tree in all respects.

SUMMARY OF THE VARIETY

The present variety of almond tree is, characteristically, open, large, vigorous, and upright; foliated with medium size, acuminate, acutely pointed leaves having a crenate margin, and alternate, small, globose, green glands; blooms early and heavily with white flowers; and is a regular, very heavy bearer of early-in-harvest, well-distributed nuts; the nuts, of medium size, being ovate, plump, soft shell, and well-sealed, and the kernels, of small but uniform size, being ovate, medium thick, and attractive in appearance.

The present variety of almond tree—which is quite similar to the Mission in tree growth, having vigorous, upright branches with acute-angle crotches—is, in distinction, further and more particularly characterized:

By an early bloom-time which is two to three days earlier than the Mission and substantially the same as the Nonpareil. This assures of effective pollen exchange throughout the full bloom-time of both the present variety and the Nonpareil; these varieties being compatible as pollenizers.

By a harvest period which is about two weeks earlier than the Mission; this frequently being of advantage because of better weather conditions and timely harvesting.

By a nut having a shell which is soft, and relatively lightweight, yet tightly sealed; this in contrast to the hard, heavier shell of the Mission. The lightweight of the shell of the nut of the present variety is evidenced by the kernel representing approximately 57% of the nut weight.

By a nut whose small but uniform size, plump, attractive kernels are of a dimension with the maximum thickness further from the base than the Mission; and By a nut whose kernel is easily blanched, while the Mission kernel is not.

BRIEF DESCRIPTION OF THE DRAWING

The drawing is an illustration, by photographic reproduction in color, of a twig with leaves and nuts; a separate leaf spray; separate nuts; and separate kernels.

DESCRIPTION OF THE VARIETY

The botanical details of this new and distinct variety of almond tree—with color definitions (except those in common color terms) referenced to Maerz and Paul Dictionary of Color (First Edition)—are as follows:

Tree:
- *Density.*—Open.
- *Size.*—Large.
- *Vigor.*—Vigorous.

Trunk:
- *Form.*—Medium.
- *Texture.*—Medium.

Branches:
- *Form.*—Slender.
- *Texture.*—Smooth.
- *Lenticels.*—Numerous. Large.

*Branching habit.*—Upright.

*Color.*—New wood — Dull brown. Mature wood — Dull brown.

Foliage:

*Quantity.*—Medium.

Leaves:

*Size.*—Medium. Average length — 3.81". Average width — 0.98".

*Shape.*—Acuminate. Acutely pointed.

*Thickness.*—Thin.

*Texture.*—Smooth.

*Margin.*—Crenate.

*Petiole.*—Medium length. Slender.

*Glands.*—Average number — 2. Alternate. Small. Globose. Green. Positioned on petiole adjacent blade.

Color.—Top side — Medium green (22-K-8). Under side — Lighter green (22-I-7).

Bloom:

*Amount of bloom.*—Heavy.

*Color.*—Pink in bud stage. White in full bloom.

*Blooming period.*—Early. 2 or 3 days earlier than Mission.

Crop:

*Bearing.*—Regular bearer.

*Productivity.*—Very heavy.

*Distribution of nuts on tree.*—Well distributed.

*Harvest period.*—September 15th–20th. Early — about 2 weeks earlier than the Mission.

*Tenacity.*—Hangs well on tree. Easy to harvest. Easy to hull.

Hull:

*Outer surface.*—Smooth.

*Form.*—Regular.

*Thickness.*—Thin.

*Flesh.*—Tough.

*Suture.*—Ridged.

*Color.*—Medium green (21-J-5) shading to silvery green (21-F-3).

*Pubescence.*—Moderate. Silvery.

*Dehiscence.*—Opens freely.

*Splitting.*—Along suture. Freely at base.

Nut:

*Size.*—Medium. Average length — 30 mm. Average width — 19 mm. Average thickness — 16 mm. Average weight — 14.4 per ounce.

*Form.*—Length/Width — Ovate. Width/Thickness — Plump.

*Shell.*—Soft. Thick. Smooth. Outer shell — Crumbling. Inner shell — Hard. Well sealed.

*Color.*—Beige (11-H-5).

*Pits.*—Large. Numerous. Deep. Round.

*Base.*—Square.

*Stem scar.*—Large. Acute.

*Apex.*—Acute. Acuminate. Tip slightly recurved.

*Wing.*—Narrow. Thin. Tapered toward base.

*Inner surface.*—Medium colored.

*Ventral streak.*—Light. Narrow. Long. Point acute. Corky.

*Percentage of kernel to nut.*—57%.

Kernel:

*Size.*—Small. Average length — 21.20 mm. Average width — 11.30 mm. Average thickness — 8.50 mm. Average weight — 25 per ounce.

*Form.*—Length/Width — Ovate. Width/Thickness — Medium.

*Base.*—Square.

*Stem scar.*—Large. Obtuse.

*Apex.*—Acute.

*Texture.*—Furrowed.

*Pellicle.*—Thick.

*Pubescence.*—Medium.

*Color.*—Antique brown (14-K-11).

*Number of doubles.*—Medium.

*Defective kernels.*—Few blanks.

*Flavor.*—Sweet.

*Quality.*—Good.

Resistance to:

*Insects and diseases.*—No more susceptible than any usual commercial variety under same growing conditions. Few almond mites observed.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, particularly characterized by a bloom-time two or three days earlier than the Mission and substantially the same as the Nonpareil, and by a harvest period about two weeks earlier than the Mission.

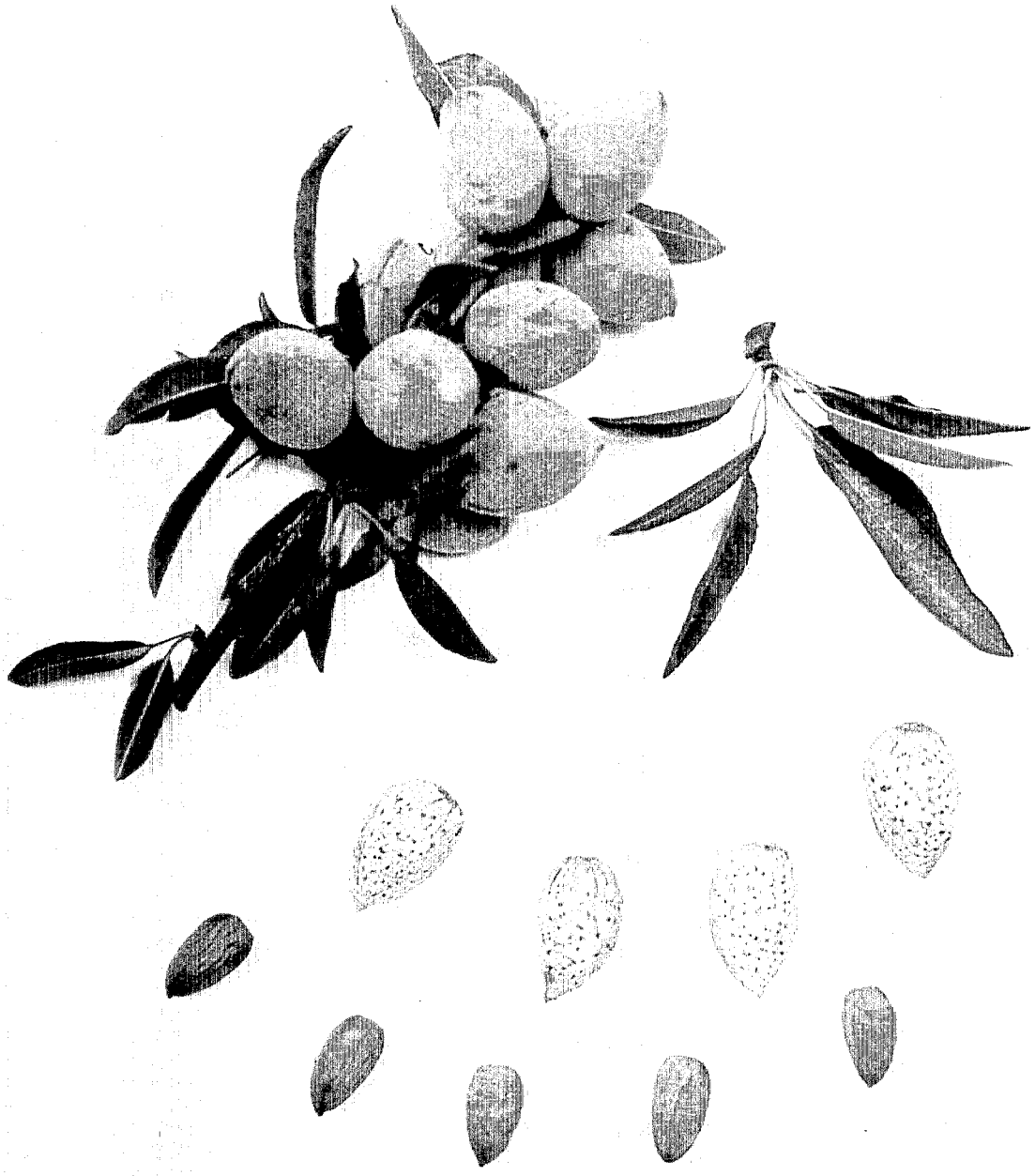

* * * * *